United States Patent [19]

Edwards

[11] 4,098,896

[45] Jul. 4, 1978

[54] 1-HALOHYDROCARBYLTHIO-3-HYDRO-CARBYLTHIO-4-SUBSTITUTED-1,2,4-DELTA²-TRIAZOLIDIN-5-ONES

[75] Inventor: Laroy H. Edwards, Napa, Calif.

[73] Assignee: Chevron Research Company, San Francisco, Calif.

[21] Appl. No.: 794,280

[22] Filed: May 5, 1977

Related U.S. Application Data

[63] Continuation-in-part of Ser. No. 617,871, Sep. 29, 1975, abandoned.

[51] Int. Cl.² .................. A01N 9/12; A61K 31/41; C07D 249/12
[52] U.S. Cl. .................. 424/269; 260/308 C
[58] Field of Search .................. 260/308 C; 424/269

[56] References Cited

U.S. PATENT DOCUMENTS

| | | | |
|---|---|---|---|
| 2,553,770 | 5/1951 | Kittleson | 260/301 |
| 2,553,773 | 5/1951 | Cohen | 260/301 |
| 3,484,451 | 12/1969 | Moon | 260/308 C |
| 3,767,666 | 10/1973 | Zielinski | 260/308 C |

OTHER PUBLICATIONS

Weygand, Organic Preparations, (Interscience, New York, 1945), p. 315.
Böhme et al., Chemical Abstracts, vol. 49, cols. 6823–6824 (1955).

*Primary Examiner*—Alton D. Rollins
*Attorney, Agent, or Firm*—D. A. Newell; T. G. DeJonghe

[57] ABSTRACT

Compounds of the formula

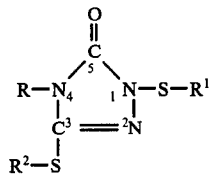

wherein R is, for example, alkyl, alkenyl, alkynyl, cycloalkyl, phenyl or substituted phenyl, $R^1$ is halo-substituted alkyl or halo-substituted alkenyl and $R^2$ is hydrocarbyl, possess fungicidal activity.

14 Claims, No Drawings

1-HALOHYDROCARBYLTHIO-3-HYDROCARBYLTHIO-4-SUBSTITUTED-1,2,4-DELTA$^2$-TRIAZOLIDIN-5-ONES

CROSS-REFERENCE TO RELATED APPLICATIONS

This application is a continuation-in-part of application Ser. No. 617,871, filed Sep. 29, 1975, now abandoned.

DESCRIPTION OF THE INVENTION

The 1-haloalkylthio or haloalkenylthio-3-alkylthio-1,2,4-delta$^2$-triazolidin-5-ones of the invention are represented by the formula

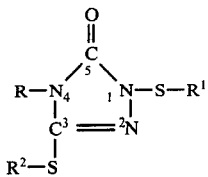

wherein
- R is alkyl of 1 to 4 carbon atoms; alkenyl of 2 to 4 carbon atoms; alkynyl of 2 to 4 carbon atoms; cycloalkyl of 3 to 8 carbon atoms; phenyl; or phenyl substituted with 1 to 3 of the same or different substituents selected from the group consisting of fluoro, chloro, bromo, alkyl of 1 to 4 carbon atoms, haloalkyl of 1 to 4 carbon atoms and 1 to 3 fluoro, bromo or chloro, alkoxy of 1 to 3 carbon atoms, and nitro; aralkyl of 7 to 14 carbon atoms, or aralkyl substituted with 1 to 3 halogen atoms from the group consisting of fluorine, chlorine and bromine;
- R$^1$ is alkyl of 1 to 4 carbon atoms substituted with 2 to 5 of the same or different halogen atoms selected from the group consisting of fluoro, chloro and bromo; or alkenyl of 2 to 4 carbon atoms substituted with 2 to 5 of the same or different halogen atoms selected from the group consisting of fluoro, chloro and bromo; and
- R$^2$ is alkyl of 1 to 4 carbon atoms; alkenyl of 2 to 4 carbon atoms; alkynyl of 2 to 4 carbon atoms; or said alkyl, alkenyl or alkynyl group substituted with 1 to 3 halogen atoms selected from the group consisting of fluorine, chlorine and bromine; aryl of 6 to 12 carbon atoms; aralkyl of 7 to 14 carbon atoms; alkaryl group of 7 to 14 carbon atoms; or said aryl, aralkyl or alkaryl group substituted with 1 to 3 halogen atoms selected from the group consisting of fluorine, chlorine and bromine, and/or a nitro group.

Preferably R is alkyl of 1 to 2 carbon atoms, more preferably methyl; alkenyl of 2 to 3 carbon atoms, more preferably allyl; cycloalkyl of 5 to 6 carbon atoms, more preferably cyclohexyl; phenyl; or phenyl substituted with 1 to 2 substituents, either the same or different, selected from fluoro, chloro, bromo and trihalomethyl where the halo is chloro, fluoro or bromo, more preferably phenyl substituted with 1 to 2 chlorine atoms or one trifluoromethyl group.

Preferably R$^1$ is alkyl of 1 to 4 carbon atoms substituted with 2 to 5 of the same or different halogen atoms selected from fluoro, chloro or bromo, and more preferably alkyl of 1 to 2 carbon atoms substituted with 3 to 4 chlorine atoms, and still more preferably trichloromethyl or 1,1,2,2-tetrachloroethyl.

Preferably R$^2$ is alkyl of 1 to 4 carbon atoms, alkenyl of 2 to 4 carbon atoms, alkynyl of 2 to 4 carbon atoms; phenyl; phenyl substituted with 1 to 5 (more preferably 1 to 3) of the same or different substituents selected from the group consisting of fluorine, chlorine, bromine, haloalkyl of 1 to 4 carbon atoms and 1 to 3 fluoro, chloro or bromo and/or a nitro group; benzyl; benzyl substituted with 1 to 3 halogen atoms from the group fluorine, chlorine and bromine and/or a nitro group. More preferably R$^2$ is alkyl of 1 to 2 carbon atoms, an alkynyl of 3 carbon atoms, a halobenzyl, or a nitrotrihalophenyl group. Most preferably R$^2$ is methyl, propargyl, p-chlorobenzyl or p-nitro-o-trifluorophenyl.

Representative alkyl groups which R may represent are methyl, ethyl, propyl, isobutyl and n-butyl. Representative alkenyl groups which R may represent are vinyl, allyl, and 2-butenyl. Representative alkynyl groups which R may represent are propargyl and 2-butynyl. Representative cycloalkyl groups which R may represent are cyclopropyl, cyclobutyl, cyclopentyl, cyclhexyl, 4-methylcyclohexyl and cyclooctyl. Representative phenyl groups which R may represent are halophenyls such as o-fluorophenyl, p-fluorophenyl, p-chlorophenyl, o-chlorophenyl, m-chlorophenyl, m-bromophenyl, 3,4-dichlorophenyl, 3-chloro-4-bromophenyl, 2,4,6-trichlorophenyl and 1,3,5-tribromophenyl; alkylphenyl such as p-tolyl, 2,4-dimethylphenyl, 3,5-diethylphenyl, 4-isopropylphenyl and 3-n-butylphenyl, haloalkylphenyl such as 2-chloromethylphenyl, 3-(1',2'-dichloroethyl)phenyl, o-trichloromethylphenyl, p-trifluoromethylphenyl, n-tribromomethylphenyl, and 2,4-di-trifluoromethylphenyl; alkoxyphenyl such as 2-methoxyphenyl, 4-ethoxyphenyl and 2,4-dipropoxyphenyl; nitrophenyl such as o-nitrophenyl and 2,4-dinitrophenyl, p-nitrophenyl and m-nitrophenyl; phenyl substituted with different substituents such as 2-nitro-4-chlorophenyl, 2-methyl-4-nitrophenyl, 3-methoxy-4-methylphenyl, 2,6-dimethyl-4-methoxyphenyl, 2-methyl-4-chlorophenyl, 2-bromo-4-ethylphenyl, and 3-chloro-4-isopropylphenyl; aralkyls such as benzyl, 2-phenylethyl, 1-phenylpropyl, p-chlorobenzyl, o-trifluoromethylbenzyl.

Representative polyhaloalkyl R$^1$ groups are difluoromethyl, dichloromethyl, dibromomethyl, dichlorofluoromethyl, trifluoromethyl, tribromomethyl, 1,2,2,2-tetrafluoroethyl, 2,2,2-trichloroethyl, 1,2,2-trichloroethyl, 2,2,2-tribromoethyl, 1,2,2,2-tetrachloroethyl, 1-bromo-2,2,2-trichloroethyl, pentachloroethyl, pentabromoethyl, 3,4-dichlorobutyl, 1,2,2,4-tetrachlorobutyl, 3,3-dichloropropyl, etc.

Representative polyhaloalkenyl R$^1$ groups are 2-chlorovinyl, 3-chloroallyl, 2-chloroallyl, 1-chloroallyl, 3,3-dichloroallyl, 3-bromoallyl, trichlorovinyl, etc.

Representative groups R$^2$ may represent are allyl groups such as methyl, ethyl, propyl, butyl, i-propyl, t-butyl, sec-butyl, etc.; alkenyl groups such as vinyl, allyl, 2-butenyl, isopropenyl, etc.; alkynyl groups such as propargyl, 2-butynyl, etc.; haloalkyl groups such as chloromethyl, dibromomethyl, trifluoromethyl, 2,2-dichloroethyl, 1,3-dibromopropyl, 2,3-dibromobutyl, 3,3-dichloropropyl, trichloromethyl, etc; haloalkenyl groups such as 1,2,2-trichlorovinyl, 3-bromo-2-propenyl, 2,3-difluoroallyl, etc.; haloalkynyl groups such as 3-chloropropargyl, 4,4,4-tribromo-2-butynyl, 2,2-difluoro-3-butynyl, 1-chloropropargyl, etc.; aryl, haloaryl and nitroaryl groups such as phenyl, 1-naphthyl, 2-naphthyl, p-biphenyl, 4-chlorophenyl, 2,4-dibromophenyl, 3,5-dichlorophenyl, 2,4,6-trichlorophenyl, 2-fluorophenyl, 2-nitrophenyl, 2-nitro-4-chlorophenyl, 3-chloro-1-naphthyl, 3-nitro-2-naphthyl, 5,6-dibromo-2-naphthyl, 2',4'-dichloro-2-fluorobiphenyl, etc.; aralkyl, haloaralkyl and nitroaralkyl groups such as benzyl, 2-phenylethyl, 2-(1'-naphthyl)propyl, 1-phenylbutyl, 4-chlorobenzyl, 2,4-dibromobenzyl, 3-(2'-fluorophenyl)butyl, 4-nitrobenzyl, 2-chloro-4-nitrobenzyl, 1-(4'-nitrophenyl)ethyl, (2-bromo-1-naphthyl)methyl, 1-methyl-2-phenylethyl, 1,1-dimethyl-2-(4'-chlorophenyl)ethyl, 2-chloro-2-phenylpropyl, etc.; alkaryl, haloalkaryl, and nitroalkaryl groups such as 3-tolyl, 4-isopropylphenyl, 2,3-dimethylphenyl, 4-ethylphenyl, 3-isopropylphenyl, 1-methyl-2-naphthyl, 4-(3'-methylphenyl)phenyl, 2-chloro-4-methylphenyl, 3,5-dibromo-4-ethylphenyl, 2-trifluoromethylphenyl, 3-chloromethylphenyl, 4-bromo-2-chloromethylphenyl, 4-nitro-3-chloromethylphenyl, 2,6-dimethyl-4-nitrophenyl, 1-chloromethyl-2-naphthyl, 4-chloromethyl-3-bromo-1-naphthyl, 3-nitro-4-methyl-2-naphthyl, 3,5-di(trifluoromethyl)phenyl, etc.

Method of Preparation

The compounds of the present invention are prepared from an appropriate 3-hydrocarbylthio-4-substituted-1,2,4-delta$^2$-triazolidin-5-one by reaction with a polyhaloalkylsulfenyl chloride, or preferably polyhaloalkenylsulfenyl chloride, thus:

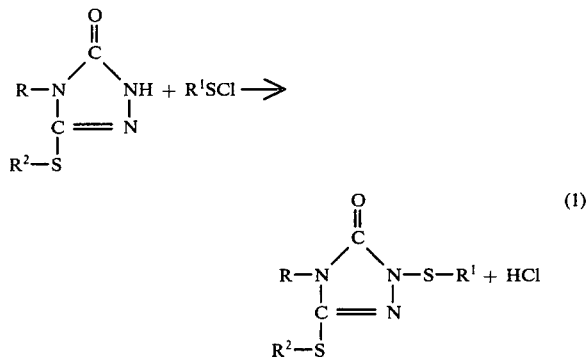

(1)

wherein R, $R^1$ and $R^2$ have the same meaning as stated before.

This reaction proceeds readily at temperatures in the range 0°–50° C, preferably 20°–40° C. Equal molar quantities of the reactants are mixed in an inert solvent, preferably a chlorinated aliphatic hydrocarbon such as chloroform, dichloroethane or dichloromethane. Dichloromethane is preferred. An equivalent amount of a base material is also present in the reaction medium to scavenge the hydrogen chloride by-product. Such bases include triethylamine, pyridine, triethylenediamine, etc. The quantity of solvent varies, but is preferably sufficient to dissolve the triazolidin-5-one. In the case of compounds having low solubility, slurries in the solvent are satisfactory. Reaction times vary from 1 to 4 hours.

The product is isolated by first washing the crude reaction product with water and then, after drying, removing the solvent by distilling under reduced pressure. The crude product obtained in this way is satisfactory for most uses. It may be further purified by chromatography or by crystallization from a benzene/hexane mixture.

An alternate method of preparation involves adding 1 equivalent of aqueous sodium hydroxide to a rapidly stirring aqueous suspension of the triazolidin-5-one at room temperature. When all of the caustic is added, the polyhaloalkylsulfenyl chloride or polyalkenylsulfenyl chloride is added rapidly and the mixture is stirred at high speed for an additional 0.1 to 1 hour. Then the reaction product is diluted with additional water to insure complete solubility of the by-product sodium chloride. The insoluble product is recovered by filtration, dried and optionally purified by crystallization from isopropanol.

The 3-hydrocarbylthio-4-substituted-1,2,4-delta$^2$-triazolidin-5-one utilized in the above reaction is in turn obtained from the cyclization of an appropriate N-[(3'-hydrocarbyl)thiouryl]methyl carbamate under the influence of a base, thus:

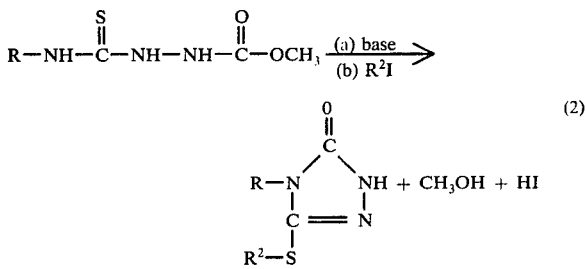

(2)

wherein R and $R^2$ are as indicated above.

The preferred base is potassium carbonate, and for satisfactory yields it is necessary that an exact equivalent (i.e., ½ mol) be used. This reaction is carried out in a polar solvent, preferably methanol or ethanol. The temperature of the reaction is in the range 50°–100° C; preferably it is the atmospheric pressure reflux temperature of the solvent. Reaction is continued until all of the carbonate has reacted, as indicated by its disappearance. Then a slight molar excess of an alkyl iodide is added. The crude reaction mixture is concentrated, mixed with water and extracted with dichloromethane. After drying, the dichloromethane is removed by distillation under reduced pressure. The crude product obtained in this way is satisfactory for the next step of the synthesis. However, it may be purified by crystallization from a benzene/hexane mixed solvent system.

The starting material for reaction (2) is readily obtained from the room-temperature reaction of methylhydrazinocarboxylate with an appropriate isothiocyanate in a solvent such as diethylether.

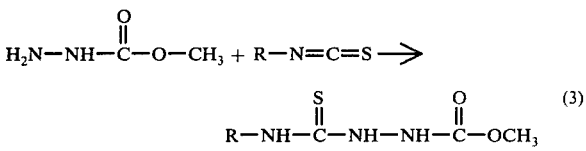

(3)

After a reaction time of 15 to 150 minutes, the product precipitates from the ether solvent and is readily recovered by cooling and filtration. No purification other than drying is required; the product is ready for use in reaction (2).

EXAMPLES

The present invention will be more fully understood by reference to the following example, which illustrates a method of preparation of the novel compounds of the present invention. This example is in no way intended to limit the invention described herein. Unless otherwise indicated, percentages are by weight.

Example 1

Preparation of 1-trichloromethylthio-3-methylthio-4-cyclohexyl-1,2,4-delta$^2$-triazolidin-5-one A 500-ml 3-necked flask equipped with a stirrer, condenser, thermometer and dropping funnel, was charged with 200 ml of dichloromethane and 7.0 g (0.0328 mol) of 3-methylthio-4-cyclohexyl-1,2,4-delta$^2$-triazolidin-5-one. When the triazolidin-5-one was all dissolved, the solution was cooled to 0° C and 4.0 g (0.04 mol) of triethylamine was added in one portion. Then 6.1 g (0.0328 mol) of trichloromethylsulfenyl chloride was added slowly because of the exothermic nature of the reaction. The resulting solution was stirred at ambient temperature for 2 hours and then at reflux for 1 hour. After cooling, the reaction mixture was washed with water, dried over magnesium sulfate and then stripped of solvent by heating under reduced pressure. The crude product was taken up in a 3:7 ether:hexane mixture and passed through a silica-gel chromatography column. After removing the solvent, there was obtained 6.0 g of 1-trichloromethylthio-3-methylthio-4-cyclohexyl-1,2,4-delta$^2$-triazolidin-5-one as an amber-colored oil. This compound was analyzed for $C_{10}H_{14}Cl_3N_3OS_2$: %Cl, calc. 29.32, found 29.4; %S, calc. 17.68, found 16.5. The infrared spectrum showed strong absorptions at 1730, 2860 and 2930 cm$^{-1}$ and sharp but medium absorptions at 715, 1240 and 1410 cm$^{-1}$.

Other compounds were prepared by the same general procedures as in the above example. These compounds are listed in Table I.

UTILITY

The compounds of the invention are useful for controlling fungi, particularly plant fungal infections caused by *Botrytis cinerea*, leaf blights caused by organisms such as *Erysiphe polygoni* and *E. chicoraciarum*, and other fungal infections caused by organisms such as *Pythrium ultimum, Helminthosporum sativum, Fusarium moniliforme, Rhizoctonia solani, Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts: alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1 to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant. Useful liquid concentrates include the emulsifiable concentrates which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

Fungicidal tests on compounds of the present invention were made using the following methods.

Example A

Tomato Late Blight

Compounds of the invention were tested for the control of the Tomato Late Blight organism *Phytophthora infestans conidia*. Five- to 6-week-old tomato (variety Bonny Best) seedlings were used. The tomato plants were sprayed with a 250-ppm solution of the test compound in acetone, water and a small amount of a non-ionic emulsifier. The sprayed plants were then inoculated one day later with the organism, placed in an environmental chamber and incubated at 66°-68° F and 100% relative humidity for at least 16 hours. Following the incubation, the plants were allowed to dry and then were maintained at 60-80% relative humidity for approximately 7 days. The percent disease control provided by a given test compound was based on the percent disease reduction relative to untreated check plants. The compounds tested and the results are tabulated in Table II.

Example B

Tomato Early Blight

Compounds of the invention were tested for the control of the Tomato Early Blight organism, *Alternaria solani conidia*. Tomato (variety Bonny Best) seedlings of 6 to 7 weeks old were used. The tomato plans were sprayed with a 250-ppm solution of the test compound in an acetone-and-water solution containing a small amount of a non-ionic emulsifier. The sprayed plants were inoculated 1 day later with the organism, dried and maintained at 60-80% relative humidity for about 12 days. Percent disease control was based on the percent disease development on untreated check plants. The compounds tested and the results are tabulated in Table III.

Example C

Celery Late Blight

Compounds of the invention were tested for the control of Celery Late Blight using celery (Utah) plants 11 weeks old. The Celery Late Blight organism was *Septoria apii*. The celery plants were sprayed with a 250-ppm solution of the candidate toxicant mixed with acetone, water and a nonionic emulsifier. The plants were then inoculated with the organism and placed in an environmental chamber and incubated at 66°-68° F in 100% relative humidity for an extended period of time (approximately 48 hours). Following the incubation, the plants were allowed to dry and then were maintained at a 60-80% relative humidity for approximately 14 days. The percent disease control provided by a given candidate toxicant is based on the percent disease reduction relative to untreated check plants. The results are reported in Table IV.

Example D

Mycelial Inhibition

Compounds of the present invention were evaluated for fungicidal effectiveness by means of a mycelial inhibition test. This test is designed to measure the fungitoxic activity of fungicidal chemicals in terms of their degree of inhibition of mycelium growth. Each compound to be tested was dissolved in acetone to 500 ppm concentration. Paper strips were innoculated with the particular mycelium growth by covering the paper with a potato dextrose broth culture of mycelial suspension. The inoculated papers were then placed on potato dextrose agar plates and sprayed by means of a microsprayer with the fungicidal solution. The treated paper strips were incubated at 25° C and data are taken after 24 hours. Fungicidal activities are measured by a zone of inhibited mycelial growth from the center of the paper strip. The effectiveness of the compounds tested for fungicidal activity is reported in Table V in terms of the micrograms/cm$^2$ for 99% control of the fungus.

Certain compounds of the present invention are also effective for controlling *Botrytis cinerea*, for example 1-(1',1',2',2'-tetrachloromethylthio)-3-methylthio-4-phenyl-1,2,4-delta$^2$-triazolidin-5-one (compound of Example 3, Table I), and 1-trichloromethylthio-3-methylthio-4-methyl-1,2,4-delta$^2$-triazolidin-5-one (compound of Example 6) were effective in controlling *Botrytis cinerea* fungus on detached horsebean leaves.

TABLE I

| Ex. No. | Compound | Melting Point, ° C | S Calc. | Cl Calc. | S Found | Cl Found |
|---|---|---|---|---|---|---|
| 1 | 1-trichloro-methylthio-3-methylthio-4-cyclohexyl-1,2,4-delta$^2$-triazolidin-5-one | — | 17.7 | 29.3 | 16.5 | 29.4 |
| 2 | 1-(1',1',2',2'-tetrachloroethylthio)-3-methylthio-4-cyclohexyl-1,2,4-delta$^2$-triazolidin-5-one | 138-140 | 15.6 | 34.5 | 15.4 | 33.7 |
| 3 | 1-(1',1',2',2'-tetrachloroethylthio)-3-methylthio-4-phenyl-1,2,4-delta$^2$-triazolidin-5-one | 128-130 | 15.8 | 35.0 | 15.4 | 34.0 |
| 4 | 1-trichloromethylthio-3-methylthio-4-phenyl-1,2,4-delta$^2$-triazolidin-5-one | 115-116 | 18.0 | 29.8 | 17.5 | 30.0 |
| 5 | 1-(1',1',2',2'-tetrachloroethylthio)-3-methylthio-4-methyl-1,2,4-delta$^2$-triazolidin-5-one | 85-87 | 18.7 | 41.3 | 17.2 | 38.9 |
| 6 | 1-trichloromethylthio-3-methylthio-4-methyl-1,2,4-delta$^2$-triazolidin-5-one | 102-104 | 21.8 | 36.1 | 21.6 | 34.6 |
| 7 | 1-(1',1',2',2'tetrachloroethylthio)-3-methylthio-4-allyl-1,2,4-delta$^2$-triazolidin-5-one | 40-42 | 17.4 | 38.4 | 16.7 | 36.2 |
| 8 | 1-trichloromethylthio-3-methylthio-4-allyl-1,2,4-delta$^2$-triazolidin-5-one | 75-77 | 20.0 | 33.2 | 19.5 | 32.6 |
| 9 | 1-trichloromethylthio-3-methylthio-4-p-chlorophenyl-1,2,4-delta$^2$-triazolidin-5-one | 142-144 | 16.4 | 36.3 | 16.2 | 35.6 |
| 10 | 1-('1,'1,2',2'-tetrachloroethylthio)-3-methylthio-4-p-chlorophenyl-1,2,4-delta$^2$-triazolidin-5-one | 140-142 | 14.6 | 40.3 | 14.2 | 40.2 |
| 11 | 1-(1',1',2',2'-tetrachloroethyl- | | | | | |

TABLE I-continued

| Ex. No. | Compound | Melting Point, °C | S Calc. | Cl Calc. | S Found | Cl Found |
|---|---|---|---|---|---|---|
|  | thio)-3-methylthio-4-m-trifluoromethylphenyl-1,2,4-delta$^2$-triazolidin-5-one | 92–93 | 13.6 | 30.0 | 14.0 | 30.4 |
| 12 | 1-trichloromethylthio-3-methylthio-4-m-trifluoromethylphenyl-1,2,4-delta$^2$-triazolidin-5-one | 145–147 | 15.1 | 25.0 | 15.5 | 23.5 |
| 13 | 1-trichloromethythio-3-methylthio-4-o,p-dichlorophenyl-1,2,4-delta$^2$-triazolidin-5-one | 115–116 | 15.1 | 41.7 | 15.1 | 39.9 |
| 14 | 1-(1',1',2',2'-tetrachloroethylthio)-3-methylthio-4-o,p-dichlorophenyl-1,2,4-delta$^2$-triazolidin-5-one | 130–132 | 13.5 | 44.9 | 13.7 | 44.0 |
| 15 | 1-(1',1',2',2'-tetrachloroethylthio)-3-methylthio-4-(3',5'-dichlorophenyl)-1,2,4-delta$^2$-triazolidin-5-one | 126–128 | 13.5 | 44.9 | 13.7 | 43.3 |
| 16 | 1-trichloromethylthio-3-methylthio-4-(3',5'-dichlorophenyl)-1,2,4-delta$^2$-triazolidin-5-one | 177–179 | 15.1 | 41.7 | 14.8 | 40.0 |
| 17 | 1-trichloromethylthio-3-methylthio-4-(2'-methyl,-4'-chlorophenyl)-1,2,4-delta$^2$-triazolidin-5-one | 131–132 | 15.8 | 35.0 | 14.9 | 36.3 |
| 18 | 1-(1',1',2',2'-tetrachloroethylthio-3-methylthio-4-(2'-methyl-4'-chlorophenyl)-1,2,4-delta$^2$-triazolidin-5-one | 142–144 | 14.1 | 39.1 | 13.0 | 39.5 |
| 19 | 1-trichloromethylthio-3-propargylthio-4-methyl-1,2,4-delta$^2$-triazolidin-5-one | 104–106 | 20.1 | — | 19.8 | — |
| 20 | 1-(1',1',2',2'-tetrachloroethylthio)-3-propargylthio-4-methyl-1,2,4-delta$^2$-triazolidin-5-one | 81–83 | 17.5 | — | 16.1 | — |
| 21 | 1-trichloromethylthio-3-(4'-chlorobenzylthio)-4-methyl-1,2,4-delta$^2$-triazolidin-5-one | 92–93 | 15.8 | 35.0 | 16.2 | 33.0 |
| 22 | 1-(1',1',2',2'-tetrachloroethylthio)-3-(4'-chlorobenzylthio)-4-methyl-1,2,4-delta$^2$-triazolidin-5-one | 104–105 | 14.1 | 39.1 | 14.4 | 38.0 |
| 23 | 1-trichloromethylthio-3-(2'-trifluoromethyl-4'-nitriophenylthio)-4-methyl-1,2,4-delta$^2$-triazolidin-5-one | 163–165 | 13.6 | 22.6 | 13.1 | 20.2 |
| 24 | 1-(1',1',2',2'-tetrachloroethylthio)-3-(2'-trifluoromethyl-4'-nitrophenylthio)-4-methyl-1,2,4-delta$^2$-triazolidin-5-one | 138–140 | 12.4 | 27.4 | 12.9 | 28.3 |

TABLE II

| Example No. | Tomato Late Blight % Control |
|---|---|
| 1 | 42 |
| 2 | 95 |
| 9 | 50 |
| 10 | 50 |
| 11 | 71 |
| 12 | 50 |
| 13 | 71 |
| 14 | 71 |
| 17 | 91 |
| 18 | 99 |
| 19 | 96 |
| 20 | 98 |
| 21 | 88 |
| 22 | 88 |
| 23 | 35 |
| 24 | 64 |

TABLE III

| Example No. | Tomato Early Blight % Control |
|---|---|
| 1 | 94 |
| 2 | 100 |
| 7 | 75 |
| 9 | 56 |
| 10 | 88 |
| 11 | 79 |
| 12 | 69 |
| 13 | 97 |
| 14 | 97 |
| 15 | 97 |
| 17 | 63 |
| 18 | 95 |
| 19 | 0 |
| 20 | 100 |
| 21 | 0 |
| 22 | 98 |
| 23 | 44 |
| 24 | 0 |

TABLE IV

| Example No. | Celery Late Blight % Control |
|---|---|
| 1 | 80 |
| 2 | 89 |
| 3 | 81 |
| 4 | 88 |
| 5 | 98 |
| 7 | 56 |
| 9 | 63 |
| 10 | 63 |
| 11 | 95 |
| 14 | 97 |
| 15 | 91 |
| 17 | 0 |
| 18 | 91 |
| 19 | 51 |
| 20 | 99 |
| 21 | 68 |
| 22 | 89 |
| 23 | 0 |
| 24 | 85 |

TABLE V

| Mycelia Inhibition, micrograms/cm² for 99% control | | | | |
|---|---|---|---|---|
| Example No. | P | R | A | F |
| 1 | >1.7 | 0.14 | 0.21 | >1.7 |
| 2 | >1.7 | 0.12 | 0.15 | 0.92 |
| 3 | 1.1 | 0.27 | 0.27 | 0.58 |
| 4 | 0.67 | 0.45 | 0.24 | 1.6 |
| 5 | 0.34 | 0.21 | 0.58 | 0.82 |
| 6 | 0.48 | 0.22 | 0.78 | >1.7 |
| 7 | 0.33 | 0.15 | 0.33 | 0.45 |
| 8 | 0.17 | 0.12 | 0.37 | 0.73 |
| 9 | >1.7 | 0.33 | 1.6 | >1.7 |
| 10 | >1.7 | 0.37 | >1.7 | >1.7 |
| 11 | 0.43 | 0.19 | 0.50 | 0.60 |
| 12 | 1.5 | 0.19 | 0.65 | >1.7 |
| 13 | >1.7 | 0.70 | 0.58 | >1.7 |
| 14 | 1.1 | 0.68 | 0.92 | 1.2 |
| 15 | >1.7 | 0.73 | 0.60 | 1.1 |
| 16 | >1.7 | 0.46 | 0.54 | 0.92 |
| 17 | 0.92 | 0.21 | 0.63 | 1.6 |
| 18 | 1.6 | 0.19 | 0.45 | 0.78 |
| 19 | >1.7 | >1.7 | >1.7 | >1.7 |
| 20 | >1.7 | 0.65 | 0.50 | 0.63 |
| 21 | >1.7 | >1.7 | 1.6 | >1.7 |
| 22 | >1.7 | 0.98 | 1.1 | 0.92 |
| 23 | 1.2 | 0.37 | 1.1 | 1.4 |
| 24 | >1.7 | 0.17 | 0.92 | 0.68 |

P = *Pythium ultimum*
R = *Rhizoctonia solani*
A = *Aspergillus niger*
F = *Fusarium moniloforma*

What is claimed is:
1. A compound of the formula

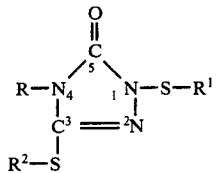

wherein

R is alkyl of 1 to 4 carbon atoms; alkenyl of 2 to 4 carbon atoms; alkynyl of 2 to 4 carbon atoms; cycloalkyl of 3 to 8 carbon atoms; phenyl; or phenyl substituted with 1 to 3 of the same or different substituents selected from the group consisting of fluoro, chloro, bromo, alkyl of 1 to 4 carbon atoms, haloalkyl of 1 to 4 carbon atoms and 1 to 3 fluoro, bromo or chloro, alkoxy of 1 to 3 carbon atoms, and nitro; aralkyl of 7 to 14 carbon atoms, or aralkyl substituted with 1 to 3 halogen atoms from the group consisting of fluorine, chlorine and bromine;

$R^1$ is alkyl of 1 to 4 carbon atoms substituted with 2 to 5 of the same or different halogen atoms selected from the group consisting of fluoro, chloro and bromo; or alkenyl of 2 to 4 carbon atoms substituted with 2 to 5 of the same or different halogen atoms selected from the group consisting of fluoro, chloro and bromo; and $R^2$ is alkyl of 1 to 4 carbon atoms; alkenyl of 2 to 4 carbon atoms; alkynyl of 2 to 4 carbon atoms; or said alkyl, alkenyl or alkynyl group substituted with 1 to 3 halogen atoms selected from the group consisting of fluorine, chlorine and bromine; aryl of 6 to 12 carbon atoms; aralkyl of 7 to 14 carbon atoms; alkaryl group of 7 to 14 carbon atoms; or said aryl, aralkyl or alkaryl group substituted with 1 to 3 halogen atoms selected from the group consisting of fluorine, chlorine and bromine, and/or a nitro group.

2. The compound of claim 1 wherein R is alkyl of 1 to 2 carbon atoms; alkenyl of 2 to 3 carbon atoms; cycloalkyl of 5 to 6 carbon atoms; phenyl; or phenyl substituted with 1 to 2 of the same or different substituents selected from fluoro, chloro, bromo and trihalomethyl, where the halo is fluoro, chloro or bromo.

3. The compound of claim 2 wherein $R^1$ is alkyl of 1 to 4 carbon atoms substituted with 2 to 5 of the same or different halogen atoms selected from fluoro, chloro and bromo.

4. The compound of claim 3 wherein $R^2$ is alkyl of 1 to 4 carbon atoms; alkenyl of 2 to 4 carbon atoms; alkynyl of 2 to 4 carbon atoms; phenyl; phenyl substituted with 1 to 3 of the same or different substituents selected from the group consisting of fluorine, chlorine, bromine, haloalkyl of 1 to 4 carbon atoms and 1 to 3 fluoro, chloro or bromo, and/or a nitro group; benzyl; benzyl substituted with 1 to 3 halogen atoms selected from the group consisting of fluorine, chlorine and bromine and/or a nitro group.

5. The compound of claim 4 wherein R is methyl, allyl, cyclohexyl, phenyl, or phenyl substituted with 1 to 2 chlorine atoms, or 1 trifluoromethyl group.

6. The compound of claim 5 wherein $R^1$ is alkyl of 1 to 2 carbon atoms substituted with 3 to 4 chlorine atoms.

7. The compound of claim 6 wherein $R^1$ is trichloromethyl or 1,1,2,2-tetrachloroethyl.

8. The compound of claim 2 wherein $R^2$ is alkyl of 1 to 2 carbon atoms.

9. The compound of claim 8 wherein $R^2$ is methyl.

10. The compound of claim 1 wherein R is methyl, allyl, cyclohexyl, phenyl or phenyl substituted with 1 to 2 chlorine atoms or 1 trifluoromethyl group; $R^1$ is trichloromethyl or 1,1,2,2-tetrachloroethyl; and $R^2$ is methyl.

11. The compound of claim 1 wherein R is methyl; $R^1$ is 1,1,2,2-tetrachloroethyl; and $R^2$ is methyl.

12. A fungicidal composition comprising a fungicidally effective amount of the compound of claim 1 and an inert carrier.

13. A method for controlling fungi which comprises contacting said fungi with a fungicidal amount of the compound of claim 1.

14. A fungicidal composition comprising a fungicidally effective amount of the compound of claim 11 and an inert carrier for the compound.

* * * * *